US 11,413,069 B2

(12) United States Patent
Einarsson

(10) Patent No.: US 11,413,069 B2
(45) Date of Patent: Aug. 16, 2022

(54) FUNCTIONAL UTERINE MANIPULATOR

(71) Applicant: The Brigham and Women's Hospital, Inc., Boston, MA (US)

(72) Inventor: Jon Einarsson, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/210,703

(22) Filed: Mar. 24, 2021

(65) Prior Publication Data

US 2021/0204980 A1 Jul. 8, 2021

Related U.S. Application Data

(63) Continuation of application No. 16/917,120, filed on Jun. 30, 2020, which is a continuation of application No. 15/463,743, filed on Mar. 20, 2017, now Pat. No. 10,722,266, which is a continuation of application No. 14/463,798, filed on Aug. 20, 2014, now Pat. No. 9,629,660, which is a continuation-in-part of application No. 14/375,200, filed as application No. PCT/US2012/065584 on Nov. 16, 2012, now Pat. No. 10,016,219.

(Continued)

(51) Int. Cl.
  *A61B 17/42* (2006.01)
  *A61B 34/00* (2016.01)
  *A61B 17/32* (2006.01)

(52) U.S. Cl.
  CPC .............. *A61B 17/42* (2013.01); *A61B 17/32* (2013.01); *A61B 17/4241* (2013.01); *A61B 34/70* (2016.02); *A61B 2017/4216* (2013.01); *A61B 2017/4225* (2013.01)

(58) Field of Classification Search
  CPC ..... A61B 17/32; A61B 17/42; A61B 17/4241; A61B 2017/4216; A61B 2017/4225; A61B 2017/4233
  See application file for complete search history.

(56) References Cited

U.S. PATENT DOCUMENTS 670,231 A * 3/1901 Heylman ................ A47L 11/33
                                                    403/94
975,581 A * 11/1910 Stevens .................... G01B 3/06
                                                    403/93

(Continued)

FOREIGN PATENT DOCUMENTS

EP 0229620 A2 7/1987
RU 2036669 C1 6/1995

(Continued)

OTHER PUBLICATIONS

USPTO. PCT International Search Report and Written Opinion dated Oct. 24, 2018, for PCT/US2018/047272, 13 pages.

(Continued)

*Primary Examiner* — Tan-Uyen T Ho
*Assistant Examiner* — Charles M Wei
(74) *Attorney, Agent, or Firm* — Winthrop & Weinstine, P.A.

(57) ABSTRACT

Implementations of a uterine manipulator operable to detach the uterus and cervix from the vagina are presented. The uterine manipulator can include a shaft, a handle, a tip assembly, and a cutting assembly.

17 Claims, 13 Drawing Sheets

Related U.S. Application Data

(60) Provisional application No. 61/592,125, filed on Jan. 30, 2012.

(56) References Cited

U.S. PATENT DOCUMENTS

| | | | | |
|---|---|---|---|---|
| 998,038 | A * | 7/1911 | Ressler | F16C 11/10 403/93 |
| 1,318,611 | A * | 10/1919 | Shaffer | F16C 7/06 74/586 |
| 2,511,234 | A * | 6/1950 | Anderson | A42B 3/145 2/8.1 |
| 2,759,261 | A * | 8/1956 | Setecka | B26D 1/547 30/116 |
| 3,452,749 | A | 7/1969 | Riedell | |
| 3,948,259 | A | 4/1976 | Bolduc et al. | |
| 4,117,609 | A * | 10/1978 | Helt | A41D 13/012 2/227 |
| 5,209,754 | A * | 5/1993 | Ahluwalia | A61B 17/0218 600/207 |
| 5,275,608 | A * | 1/1994 | Forman | A61B 17/29 606/170 |
| 5,314,445 | A * | 5/1994 | Heidmueller Degwitz | A61B 17/320016 606/174 |
| 5,381,943 | A * | 1/1995 | Allen | A61B 17/0682 227/177.1 |
| 5,409,496 | A * | 4/1995 | Rowden | A61B 17/4241 606/119 |
| 5,431,323 | A * | 7/1995 | Smith | A61B 17/0682 227/177.1 |
| 5,487,377 | A * | 1/1996 | Smith | A61B 17/4241 600/204 |
| 5,520,698 | A * | 5/1996 | Koh | A61B 17/4241 128/898 |
| 5,540,700 | A * | 7/1996 | Rowden | A61B 17/4241 600/201 |
| 5,643,285 | A * | 7/1997 | Rowden | A61B 17/4241 606/119 |
| 5,795,308 | A * | 8/1998 | Russin | A61B 10/0266 600/567 |
| 5,840,077 | A * | 11/1998 | Rowden | A61B 17/4241 606/119 |
| 5,906,579 | A | 5/1999 | Vander | |
| 5,951,465 | A * | 9/1999 | Schiff | A61B 17/4241 600/224 |
| 6,030,406 | A * | 2/2000 | Davis | A61B 17/00008 604/104 |
| 6,059,719 | A * | 5/2000 | Yamamoto | A61B 1/00059 600/104 |
| 6,156,006 | A * | 12/2000 | Brosens | A61B 17/00234 604/104 |
| 6,230,593 | B1 * | 5/2001 | Hsieh | B25G 1/005 81/177.5 |
| 6,331,166 | B1 | 12/2001 | Burbank et al. | |
| 6,464,711 | B1 * | 10/2002 | Emans | A61B 17/32002 606/167 |
| 7,824,342 | B2 * | 11/2010 | Minosawa | A61B 17/32056 600/564 |
| 8,079,963 | B2 * | 12/2011 | Rosenblatt | A61B 5/0538 600/591 |
| 8,323,278 | B2 * | 12/2012 | Brecheen | A61B 17/4241 606/45 |
| 8,460,289 | B2 | 6/2013 | Sartor | |
| 8,608,738 | B2 * | 12/2013 | Brecheen | A61B 18/1482 606/45 |
| 8,858,586 | B2 * | 10/2014 | Chang | A61B 17/320725 606/196 |
| 9,011,433 | B2 * | 4/2015 | Batchelor | A61B 18/1485 606/41 |
| 9,033,977 | B2 | 5/2015 | Morozov | |
| 9,144,454 | B2 * | 9/2015 | Batchelor | A61B 18/1485 |
| 9,629,660 | B2 * | 4/2017 | Einarsson | A61B 17/4241 |
| 10,016,219 | B2 * | 7/2018 | Einarsson | A61B 17/320016 |
| 2001/0021854 | A1 * | 9/2001 | Donnez | A61B 17/4241 606/119 |
| 2005/0240211 | A1 | 10/2005 | Sporri et al. | |
| 2008/0097467 | A1 | 4/2008 | Gruber et al. | |
| 2008/0147113 | A1 * | 6/2008 | Nobis | A61B 17/29 606/205 |
| 2009/0182329 | A1 * | 7/2009 | Dycus | A61B 18/14 606/48 |
| 2010/0228089 | A1 | 9/2010 | Hoffman et al. | |
| 2010/0228119 | A1 | 9/2010 | Brennan et al. | |
| 2012/0143209 | A1 * | 6/2012 | Brecheen | A61B 17/4241 606/119 |
| 2012/0209254 | A1 * | 8/2012 | Park | A61B 17/06061 606/1 |
| 2012/0323079 | A1 | 12/2012 | Bakare et al. | |
| 2012/0330324 | A1 * | 12/2012 | Sauer | A61B 17/4241 606/119 |
| 2013/0158428 | A1 | 6/2013 | Toth et al. | |
| 2013/0172918 | A1 * | 7/2013 | Smith | A61B 1/00137 606/170 |
| 2014/0012305 | A1 * | 1/2014 | Horton | A61L 29/126 606/193 |
| 2014/0088579 | A1 | 3/2014 | Burnett et al. | |
| 2014/0180282 | A1 * | 6/2014 | Brecheen | A61B 17/4241 606/45 |
| 2014/0276812 | A1 * | 9/2014 | Batchelor | A61B 18/1485 606/48 |
| 2014/0276916 | A1 | 9/2014 | Ahluwalia et al. | |
| 2014/0358158 | A1 | 12/2014 | Einarsson | |
| 2015/0133923 | A1 * | 5/2015 | Batchelor | A61B 18/1482 606/48 |
| 2015/0250992 | A1 * | 9/2015 | Morriss | A61M 25/0074 606/198 |
| 2015/0351621 | A1 | 12/2015 | Hill et al. | |
| 2017/0156756 | A1 * | 6/2017 | Adajar | A61B 18/082 |
| 2017/0189065 | A1 | 7/2017 | Einarsson | |
| 2017/0189066 | A1 * | 7/2017 | Parys | A61B 17/42 |
| 2018/0325552 | A1 | 11/2018 | Weihe et al. | |

FOREIGN PATENT DOCUMENTS

| | | |
|---|---|---|
| SU | 731961 A1 | 5/1980 |
| WO | 9611641 A1 | 4/1996 |
| WO | 2013115892 A1 | 8/2013 |
| WO | 2019040461 A1 | 2/2019 |
| WO | 2019040542 A1 | 2/2019 |

OTHER PUBLICATIONS

USPTO. PCT International Search Report and Written Opinion dated Dec. 11, 2018, for PCT/US2018/047402, 10 pages.

PCT International Search Report and Written Opinion, PCT/US2012/065584, dated Feb. 14, 2013, 10 pages.

* cited by examiner

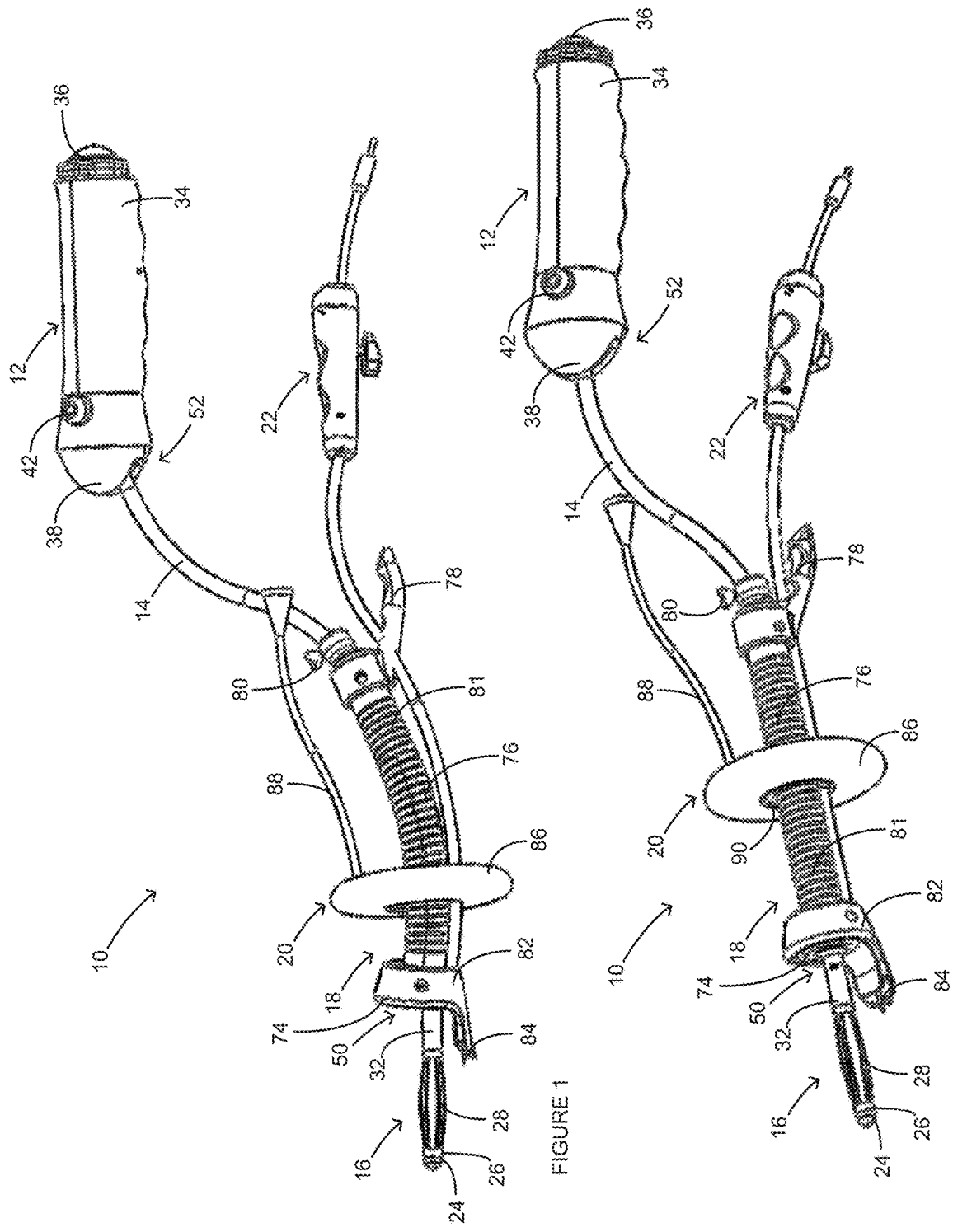

FUNCTIONAL UTERINE MANIPULATOR

CROSS-REFERENCE TO RELATED APPLICATIONS

This application is a continuation of U.S. patent application Ser. No. 16/917,120, filed Jun. 30, 2020, which in turn is a continuation of U.S. patent application Ser. No. 15/463,743, filed Mar. 20, 2017, which in turn is a continuation of U.S. application Ser. No. 14/463,798, filed Aug. 20, 2014, which is a continuation-in-part of U.S. application Ser. No. 14/375,200, filed Jul. 29, 2014, which is the National Stage of International Application No. PCT/US2012/065584, filed Nov. 16, 2012, which claims the benefit of U.S. Provisional Application No. 61/592,125, filed Jan. 30, 2012, the disclosures of which are hereby incorporated by reference in their entirety for all purposes.

BACKGROUND

The present disclosure relates generally to uterine manipulators and methods of using a uterine manipulator for detaching the uterus and cervix from the vagina.

Uterine manipulators are conventionally used as aids in laparoscopic hysterectomies to mobilize and position the uterus, to provide better visualization of the vagina and the cervix for facilitating their separation, and to remove the uterus after colpotomy is performed. Basic uterine manipulators include a handle, a shaft, an inflatable balloon, and a cervical stop. The handle is located at one side of the shaft and the inflatable balloon is located near the tip of the other side of the shaft.

The inflatable balloon is maneuvered into the uterus in an deflated condition and then inflated (e.g., via saline or water injected through the shaft) to help stabilize the uterine manipulator during the procedure and also to help remove the uterus after is has been separated from the vagina. Once the uterine manipulator is positioned, the cervical stop can be adjusted to abut the cervix.

More complex uterine manipulators include a handle, a shaft, an inflatable balloon, a cervical cup, and an occluder. The handle, the shaft, and the inflatable balloon can have similar functions as described above. The cervical cup can be fitted around the cervix and pressed inward against the vaginal fornix in order to provide an observable or palpable landmark of the incision point for dissecting the cervix and uterus from the vagina and to physically separate the incision area from the nearby ureters. Using such complex uterine manipulators, the incision for detaching the uterus and cervix from the vagina is executed laparoscopically (e.g., via a hook electrode). The occluder, positioned within the vagina when the uterine manipulator is set, makes continuous radial contact with the vaginal wall in order to maintain pneumoperitoneum after the incision between the vagina and the cervix has been made. The occluder may be a silicone cup pushed up the shaft and pressed into the vagina, or a balloon slid onto the shaft and inflated so that it presses against the vaginal wall.

Current uterine manipulators can present drawbacks in certain situations. For example, cup or balloon type occluders are in direct contact with the shaft and slid along the shaft for placement within the vagina. In some cases, this can inhibit rotation of the shaft when attempting to manipulate the position of the uterus, for example to make incisions around the fornix. In other cases, attempting to rotate the shaft can cause the occluder to slide along the shaft and disengage from the vaginal wall, resulting in a loss of pneumoperitoneum. In addition, current uterine manipulators only serve to provide guidance for detaching the uterus and the cervix from the vagina via laparoscopic tools.

Therefore, it would be desirable to have a uterine manipulator that overcomes these drawbacks.

SUMMARY

The present disclosure provides a uterine manipulator that is operable to detach the uterus and cervix from the vagina. The uterine manipulator can include an umbrella-like tip that creates a secure connection between the uterine manipulator and the uterus and cervix. The uterine manipulator can also include a pneumooccluder that permits rotation of the manipulator shaft while maintaining pneumoperitoneum. The uterine manipulator can further include a cutter that travels in a circle at the junction of the cervix and the vagina, permitting detachment of the uterus and cervix from the top of the vagina.

In accordance with one aspect of the disclosure, a uterine manipulator is provided. The uterine manipulator can be adapted for insertion into a uterus for stabilizing and repositioning the uterus during a hysterectomy, where the uterus and cervix are detached from the vagina. The uterine manipulator can include a shaft, a handle, a tip assembly, and a cutting assembly. The shaft can include a first end and a second end, and the handle can be coupled to the first end and be pivotable relative to the first end about a first axis. The tip assembly can be coupled to the second end and pivotable relative to the second end along a second axis parallel to the first axis, and can be adapted for insertion into the uterus. The cutting assembly can be coupled around the shaft and adapted to receive the cervix when the tip assembly is inserted into the uterus.

The foregoing and other advantages of the disclosed embodiments will appear from the following description. In the description, reference is made to the accompanying drawings which form a part hereof, and in which there is shown by way of illustration a preferred embodiment of the disclosure. Such embodiment does not necessarily represent the full scope of the invention, however, and reference is made therefore to the claims and herein for interpreting the scope of the disclosure.

BRIEF DESCRIPTION OF THE DRAWINGS

FIG. 1 is a perspective view of a uterine manipulator according to the present disclosure.

FIG. 2 is another perspective view of the uterine manipulator of FIG. 1.

DETAILED DESCRIPTION

Figure 12A:
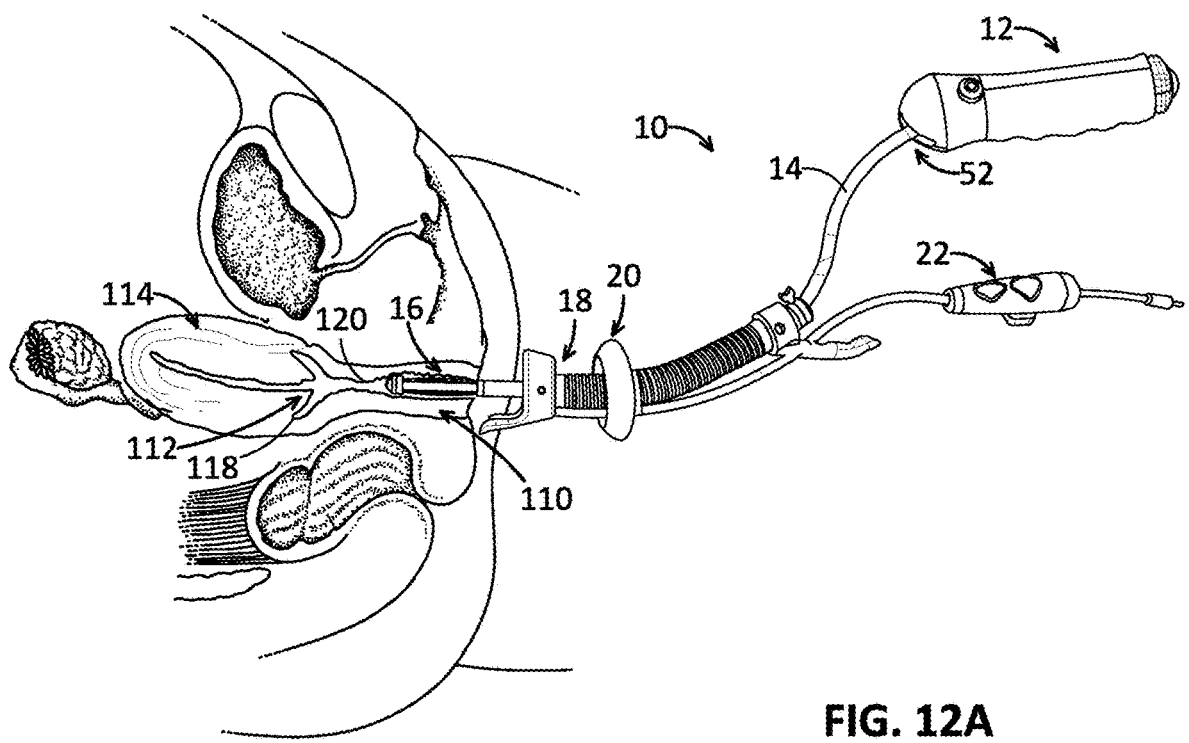
FIGS. 12A-12D are cross-sectional views of a pelvic cavity and the uterine manipulator of FIG. 1.
Figure 12B:
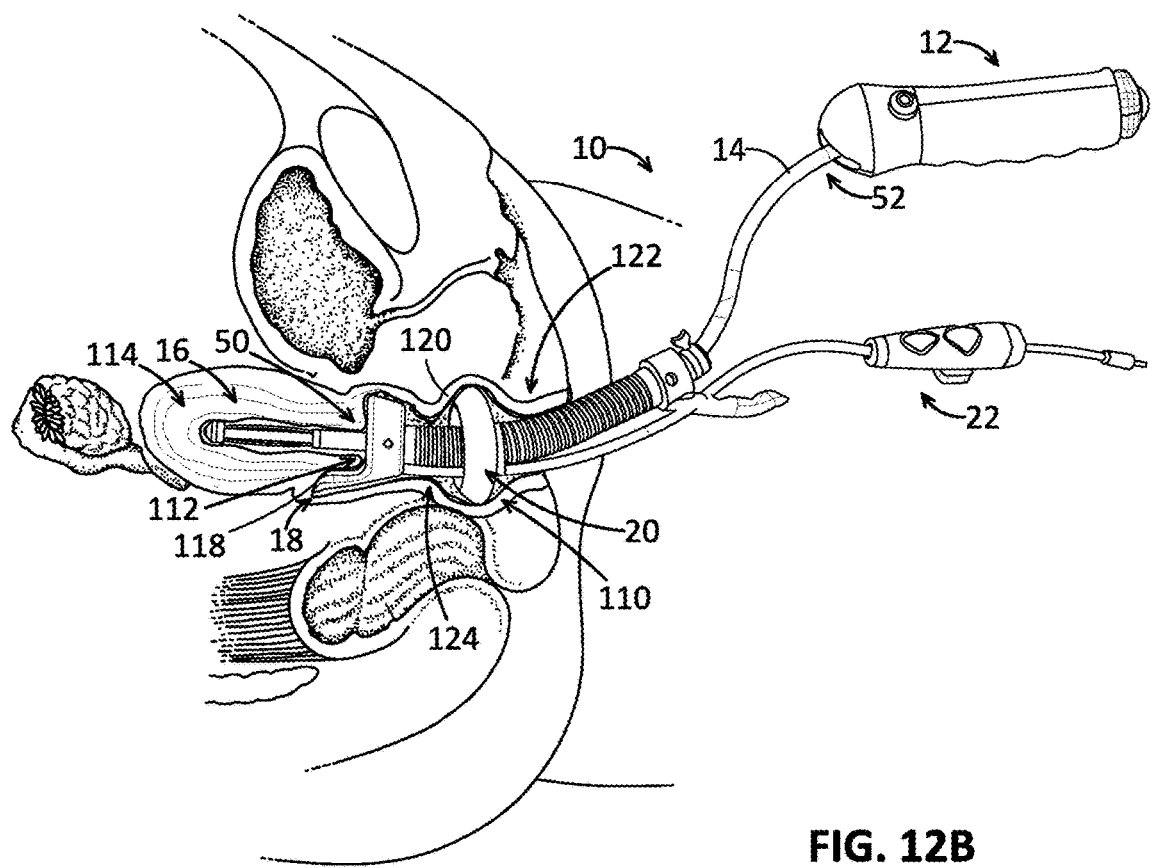
Figure 12C:
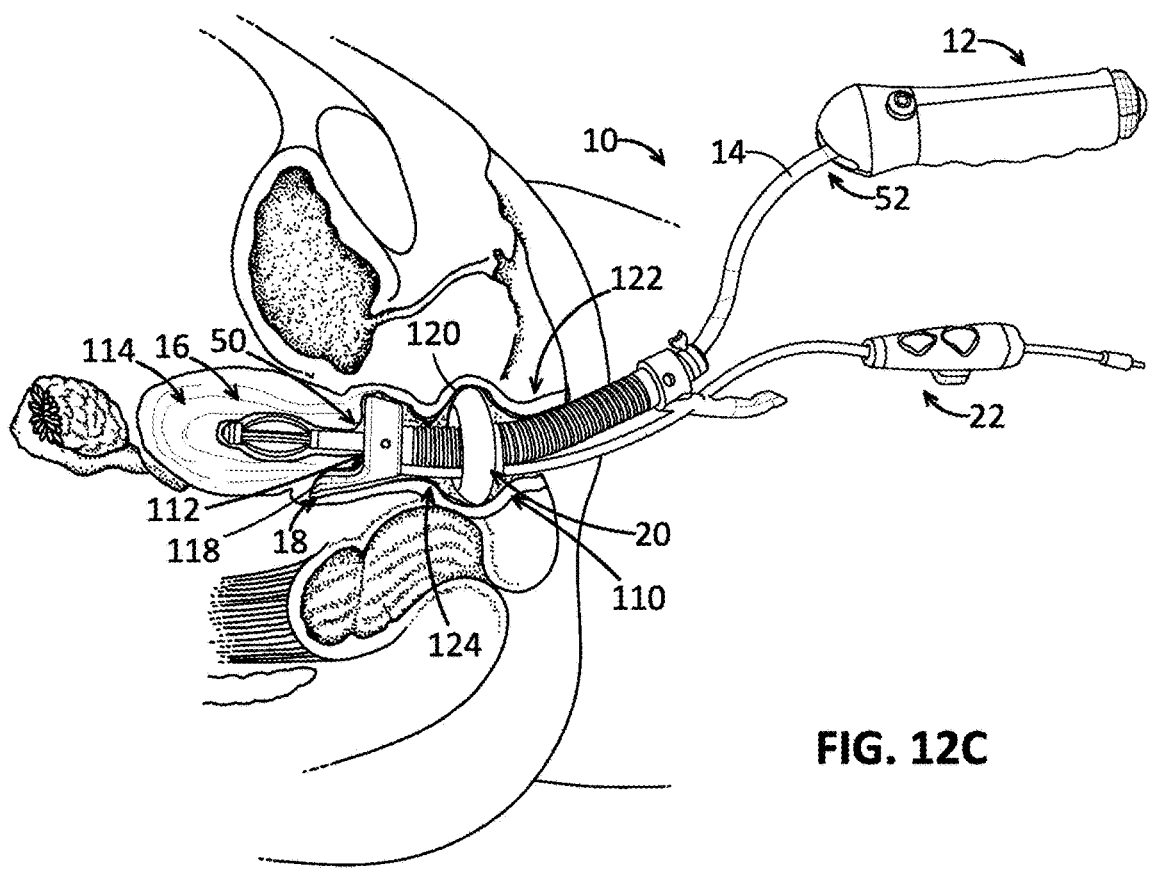

FIGS. 1 and 2 illustrate a uterine manipulator according to the present disclosure. At least one embodiment can be used in laparoscopic hysterectomies, laparoscopic myomectomies, and/or other pelvic procedures. The uterine manipulator 10 can include a handle 12, a shaft 14, a tip assembly 16, a cutting assembly 18, a pneumooccluder 20, and an electrical connector assembly 22. During use, the uterine manipulator 10 can be inserted into a patient's vagina 110, as shown in FIG. 12A, and then guided past the cervix 112 and into the uterus 114, as shown in FIG. 12B, using the handle 12. As shown in FIGS. 12B and 12C, when the uterine manipulator 10 is inserted, the tip assembly 16 can be positioned in the uterus 114, the cutting assembly 18 can be positioned adjacent to the vaginal fornix 118 and can press against the cervix 112, and the pneumooccluder 20 can be positioned inside the vagina 110.

Figure 3:
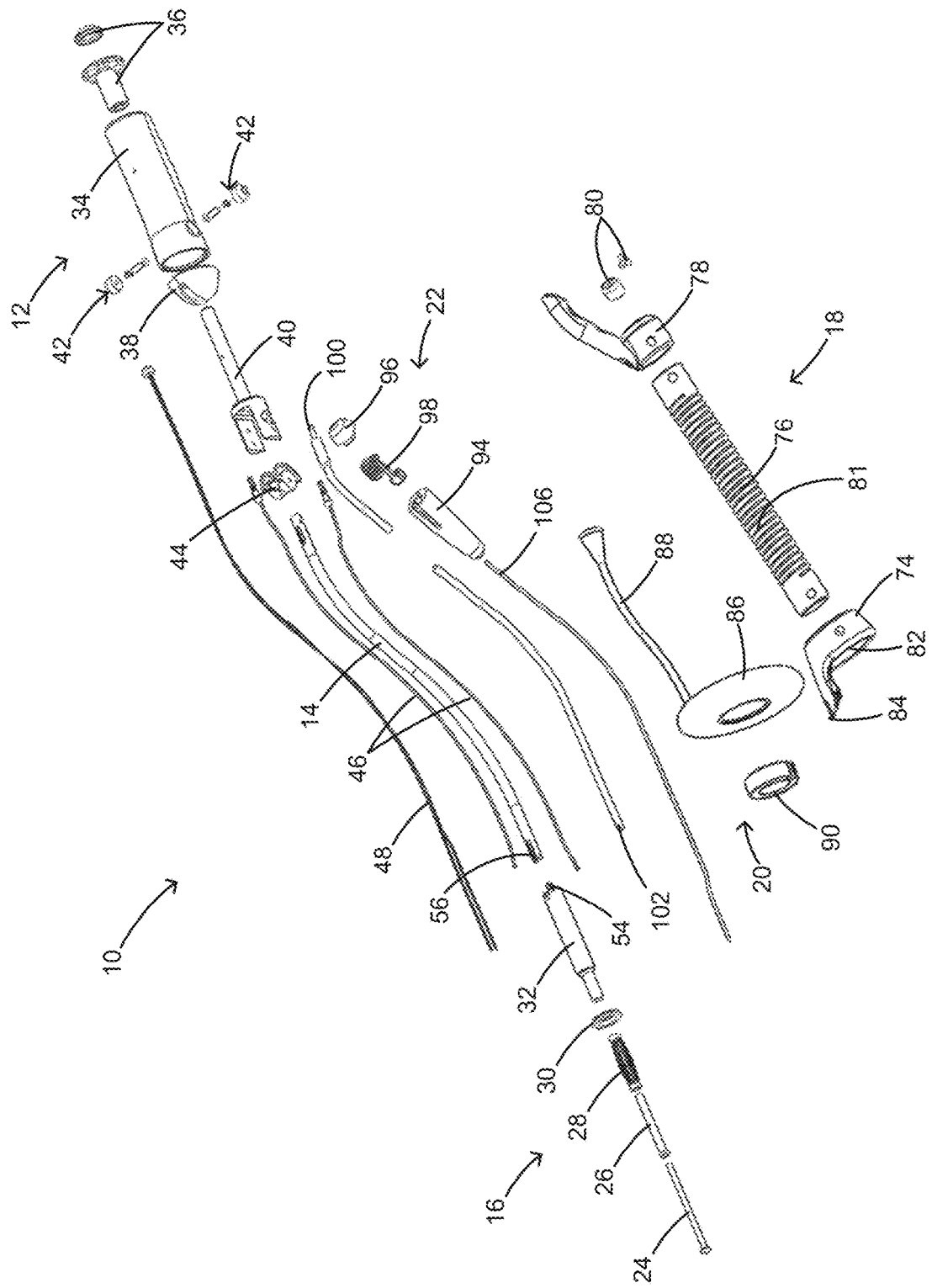
FIG. 3 is an exploded perspective view of the uterine manipulator of FIG. 1.
Figure 4A:
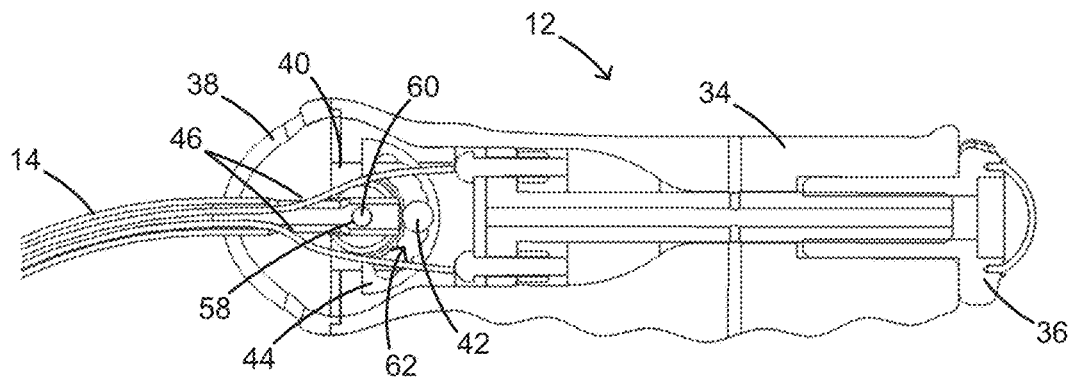
FIGS. 4A and 4B are partial side views of a handle and a tip assembly, respectively, of the uterine manipulator of FIG. 1.
Figure 4B:
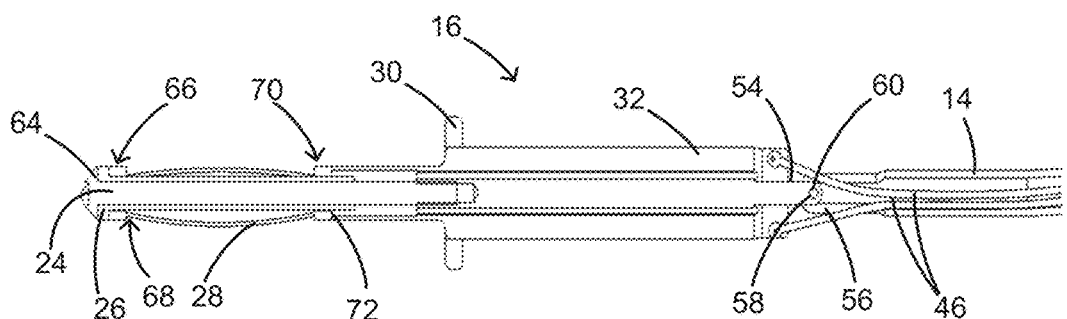

As shown in FIG. 3, the tip assembly 16 can include an expansion tip 24, a tip shaft 26, expansion elements 28, an abutment 30, and a tip housing 32, and the handle 12 can include a handle housing 34, an expansion actuator 36, a cap 38, a hinge 40, hinge pins 42, and a pivoting element 44. The shaft 14 can be coupled to the tip assembly 16 via the tip housing 32, and can be coupled to the handle 12 via the pivoting element 44. The tip assembly 16 can be coupled to the handle 12 via connectors 46. As shown in FIGS. 4A and 4B, the connectors 46 can be routed from inside the handle housing 34, through the shaft 14, and coupled to the tip housing 32.

Figure 5A:
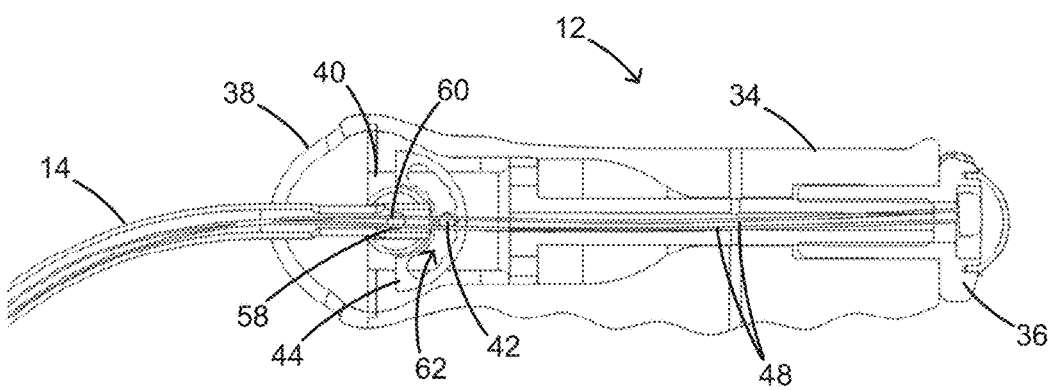
FIGS. 5A and 5B are additional partial side views of the handle and the tip assembly, respectively, of the uterine manipulator of FIG. 1.
Figure 5B:
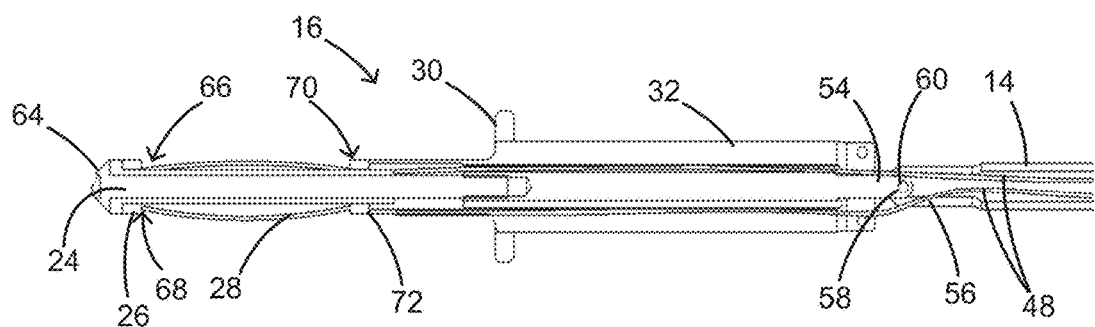

As shown in FIGS. 3, 5A and 5B, expansion connectors can be coupled to the expansion actuator 36, routed from inside the handle housing 34 through the shaft 14 and coupled to the expansion tip 24 for actuating the tip assembly 16, as further described below. In at least one embodiment, some or all of the components of the uterine manipulator 10 can be disposable. Some or all of the components can be removable from one another, for example, so that disposable components can be uncoupled from permanent components and replaced with new disposable components.

Figure 6A:
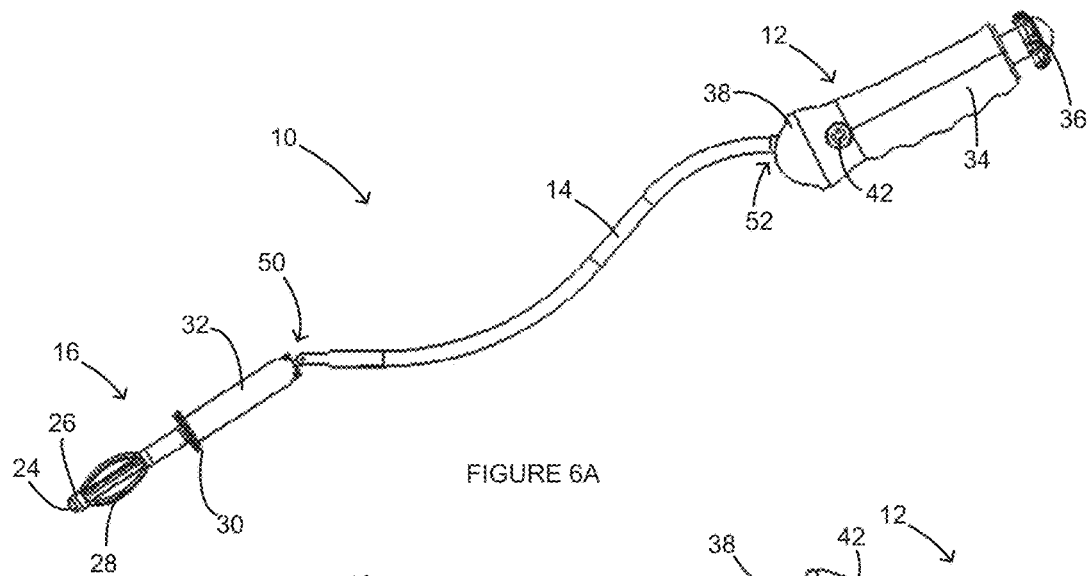
FIGS. 6A-6C are side views of the uterine manipulator of FIG. 1 in different pivoting positions.
Figure 6B:
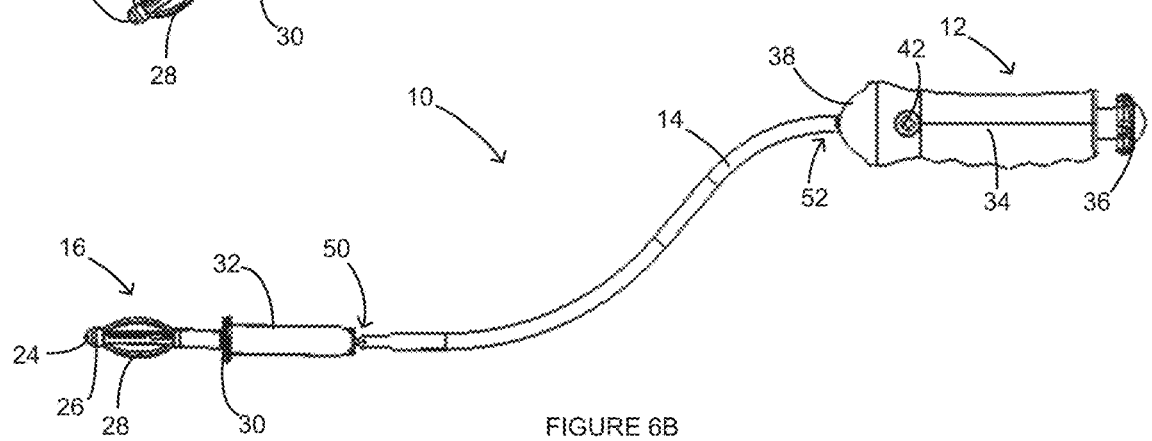
Figure 6C:
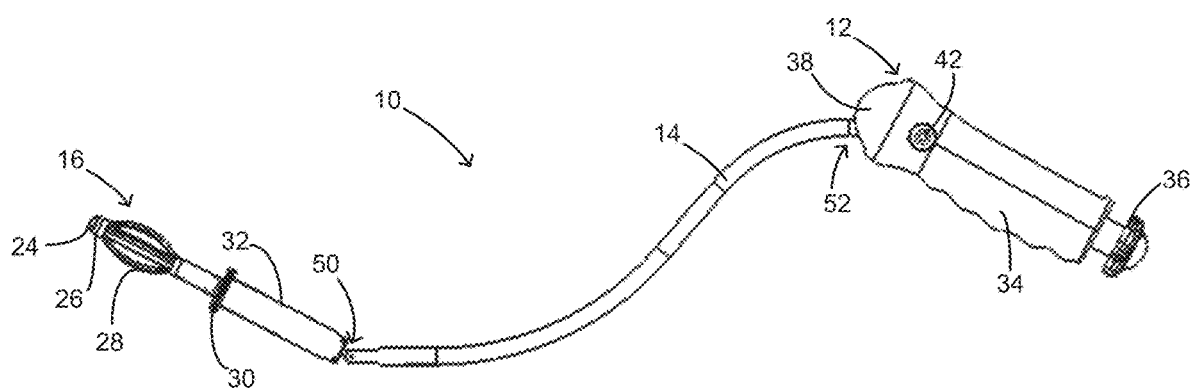
Figure 7A:
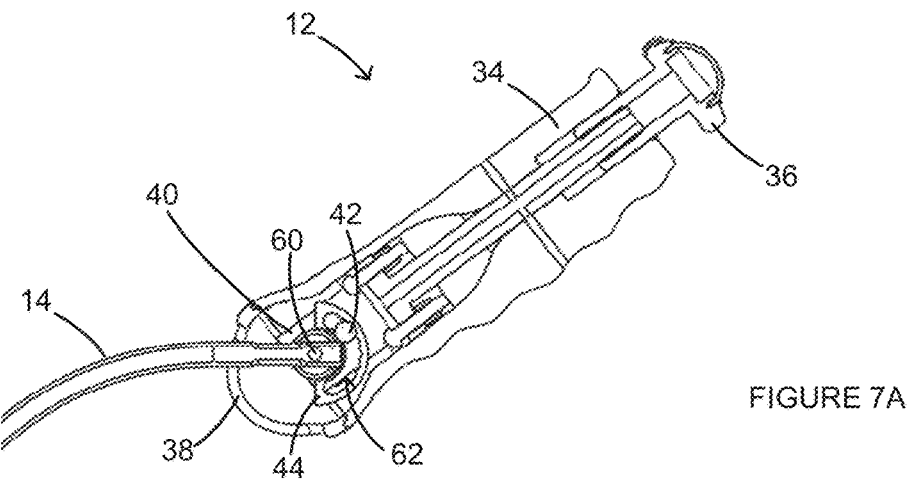
FIGS. 7A-7D are side and front views of the handle assembly of the uterine manipulator of FIG. 1 in different pivoting positions.
Figure 7B:
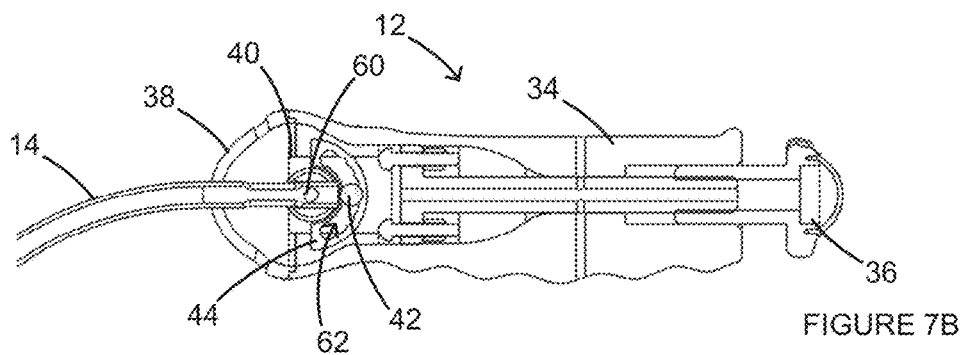
Figure 7C:
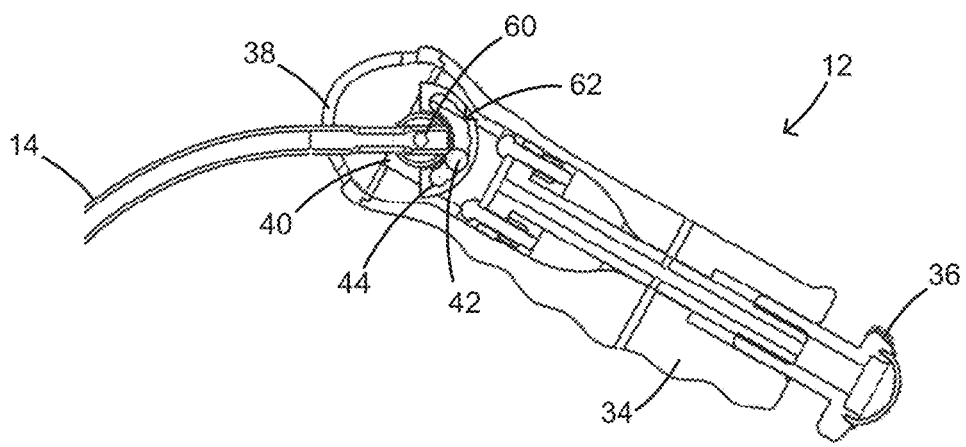
Figure 7D:
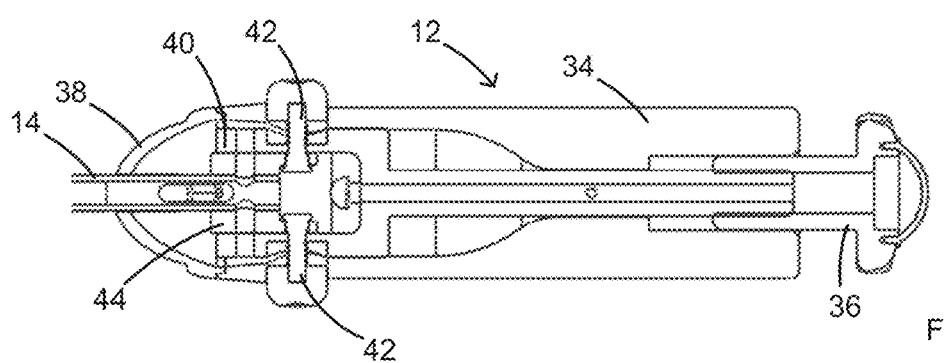

As shown in FIGS. 6A-6C, the tip assembly 16, the shaft 14, and the handle 12 can be pivotable relative to each other at two separate pivot points 50, 52. The first pivot point 5o and the second pivot point 52 can facilitate insertion of the uterine manipulator 10 into the uterus 114 and can also facilitate repositioning of the uterus 114 during a hysterectomy. The first pivot point 50 can be located at the connection between the tip housing 32 and the shaft 14. For example, as shown in FIGS. 4B and B, the end 54 of the tip housing 32 can be positioned between end components 56 of the shaft 14 so that through holes 58 in each component 54, 56 are aligned, and a pin 60 can be routed through the through holes 58 to permit a pivotable connection. The second pivot point 52 can be located at the connection between the shaft 14 and the handle 12. For example, as shown in FIGS. 4A, 5A, and 7A-7D, the shaft 14 can be fixed to the pivoting element 44 (e.g., via a pin 60 and through hole 58 connection) and the pivoting element 44 can be pivotable about the hinge 40 within the handle housing 34. The hinge pins 42 can extend through the handle housing 34, the hinge 40, and a track 62 of the pivoting element 44, as best shown in FIG. 7D. The track 62 can be ribbed so that the pivoting element 44 cannot freely slide within it. Rather, the pivoting element 44 can be substantially fixed at specific points along the ribbed track 62 and only adjusted by applying an amount of force. This can prevent unwanted movement of the second pivot point 52 unless a deliberate force is applied.

In at least one embodiment, an additional mechanism (for example, in the handle 12), can be used to control both pivot points 50, 52. For example, if the additional mechanism is actuated in a first direction, both pivot points 50, 52 can be locked in place. If the additional mechanism is actuated in a second direction, both pivot points 50, 52 can be unlocked and maneuverable. The shaft 14 can be constructed of a non-rigid, flexible material to facilitate insertion of the uterine manipulator 10 into the uterus 114.

Figure 8A:
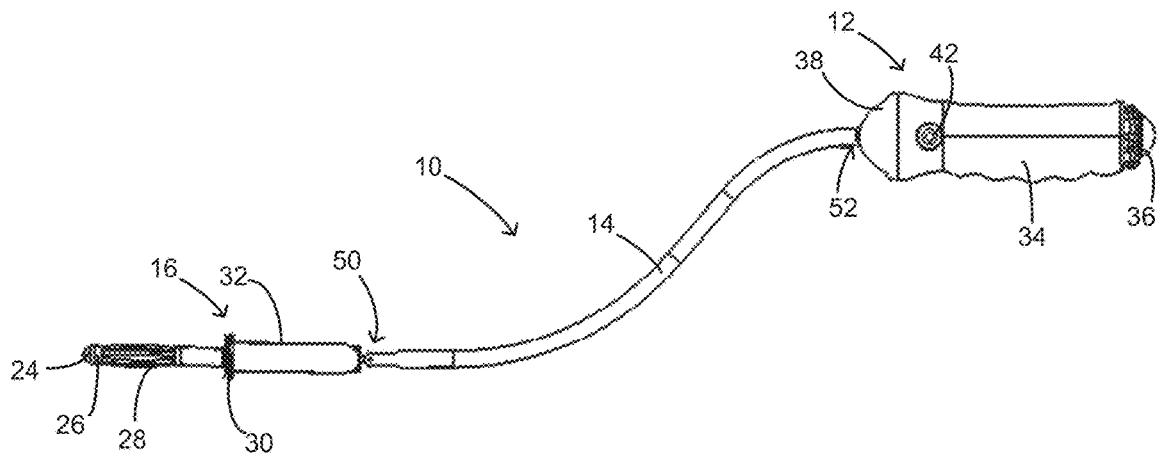
FIGS. 8A and 8B are side views of the uterine manipulator of FIG. 1 in a retracted position and an expanded position, respectively.
Figure 8B:
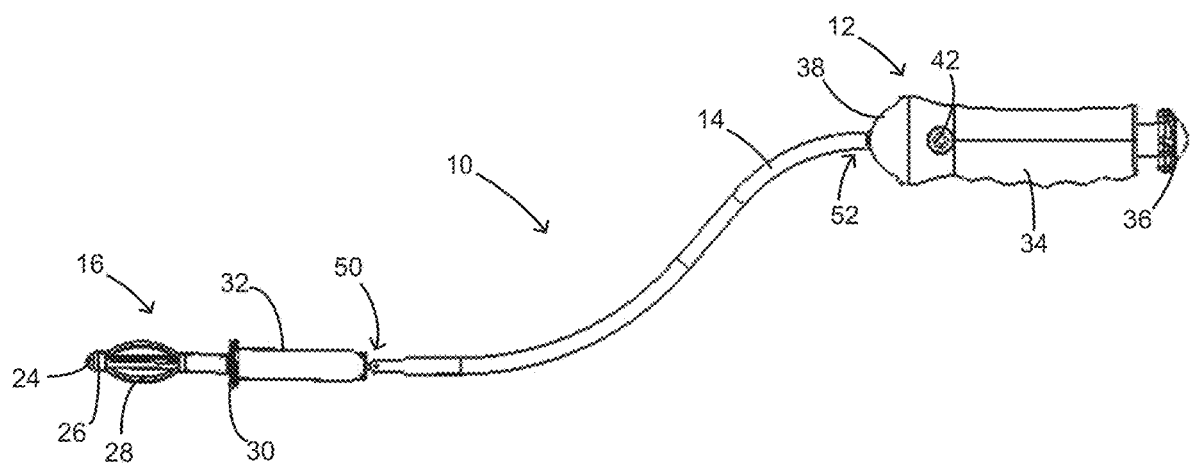
Figure 9A:
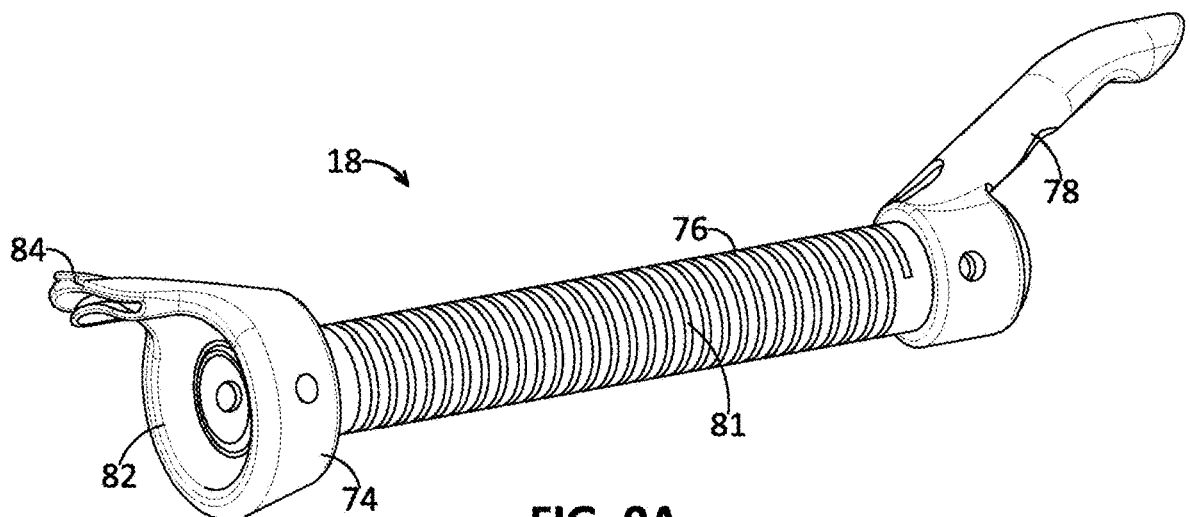
FIGS. 9A and 9B are perspective views of a cutting assembly and a backstop, respectively, of the uterine manipulator of FIG. 1.
Figure 9B:
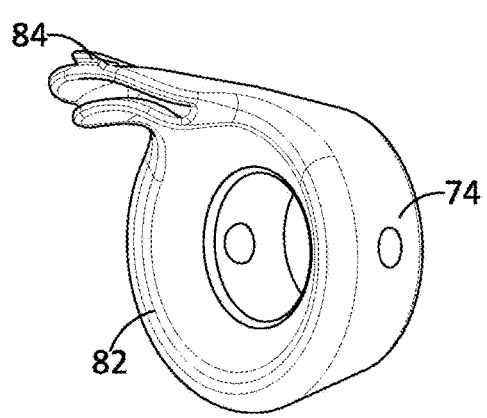

The tip assembly 16 can act as an umbrella-like expansion component capable of being adjusted between a retracted position and an expanded position. As a result, the tip assembly 16 can replace conventional intra-uterine balloon elements. The tip assembly 16 can be situated into the retracted position, as shown in FIGS. 8A and 12B, to facilitate insertion into the uterus 114 (e.g., until the abutment 30 reaches the cervix 112). Once inserted into the uterus 114, the tip assembly 16 can be deployed into the expanded position, as shown in FIGS. 8B and 12C, to facilitate a secure connection between the uterine manipulator 10 and the uterus 114 and cervix 112.

The expansion elements 28 can be spring-like elements capable of being in compression (e.g., shortened in length) and in tension (e.g., lengthened). Pulling the expansion actuator 36 away from the handle housing 34 can cause the expansion elements 28 to compress and expand outward circumferentially, situating the tip assembly 16 into the expanded position. Pushing the expansion actuator 36 back into the handle housing 34 causes the expansion elements 28 to retract back into tension and lengthen, situating the tip assembly 16 into the retracted position. Alternatively, the expansion actuator 36 can be twisted or rotated, rather than pulled and pushed from the handle housing 34, to adjust the expansion elements 28.

As shown in FIGS. 4B and 5B, the expansion tip 24 can slide into the tip shaft 26 until an end stop 64 of the expansion tip 24 reaches the end 66 of the tip shaft 26. The expansion elements 28 can fit over the tip shaft 26 until a first end 68 of the expansion elements 28 reaches the end 66 of the tip shaft 26. Both the expansion tip 24 and the tip shaft 26 can be slid into the tip housing 32, while the second end 70 of the expansion elements 28 can rest against an outer edge 72 of the tip housing 32.

Pulling the expansion actuator 36 outward from the handle housing 34 causes the expansion connectors 48 to pull the expansion tip 24, and the tip shaft 26, further into the tip housing 32. Because the expansion elements 28 rest against the edge 72 of the tip housing 32, they are compressed (i.e., shortened in length) when the expansion tip 24 and the tip shaft 26 are forced into the tip housing 32. Shortening of the expansion elements 28 causes them to expand in their circumferential direction, therefore situating the tip assembly 16 into the expanded position. In the reverse, pressing the expansion actuator 36 back into the housing releases the pulling tension of the expansion connectors 48 on the expansion tip 24. The expansion elements 28 can be in a resting state when in tension and thus, without the pulling tension by the expansion connectors 48, the expansion elements 28 will revert back to their resting, retracted state, thereby pulling the expansion tip 24 and the tip shaft 26 back out from the tip housing 32 and situating the tip assembly 16 into the retracted position.

Figure 10A:
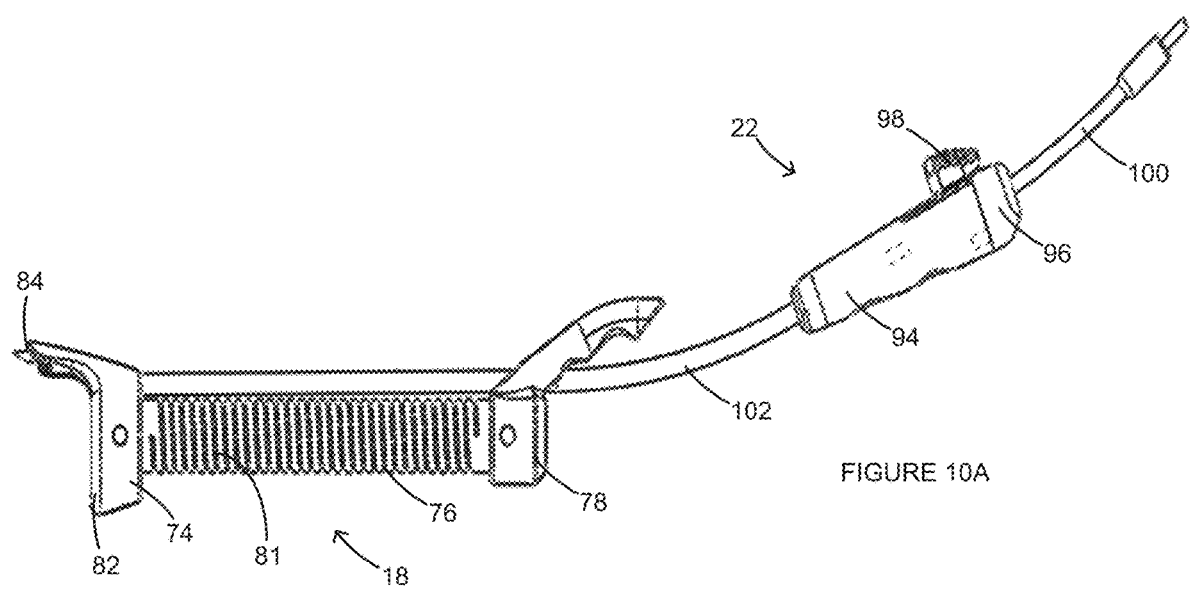
FIGS. 10A and 10B are side views of the cutting assembly and an electrical connector assembly, respectively, of the uterine manipulator of FIG. 1.
Figure 10B:
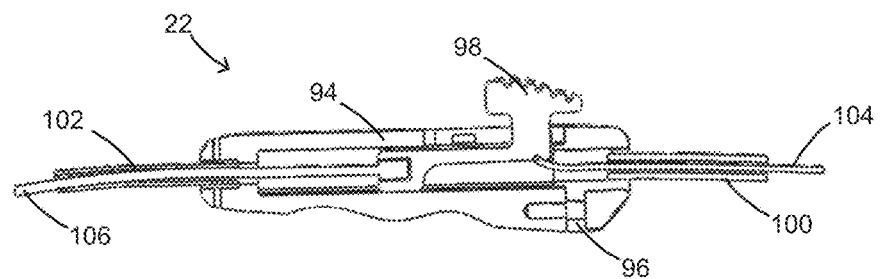
Figure 12D:
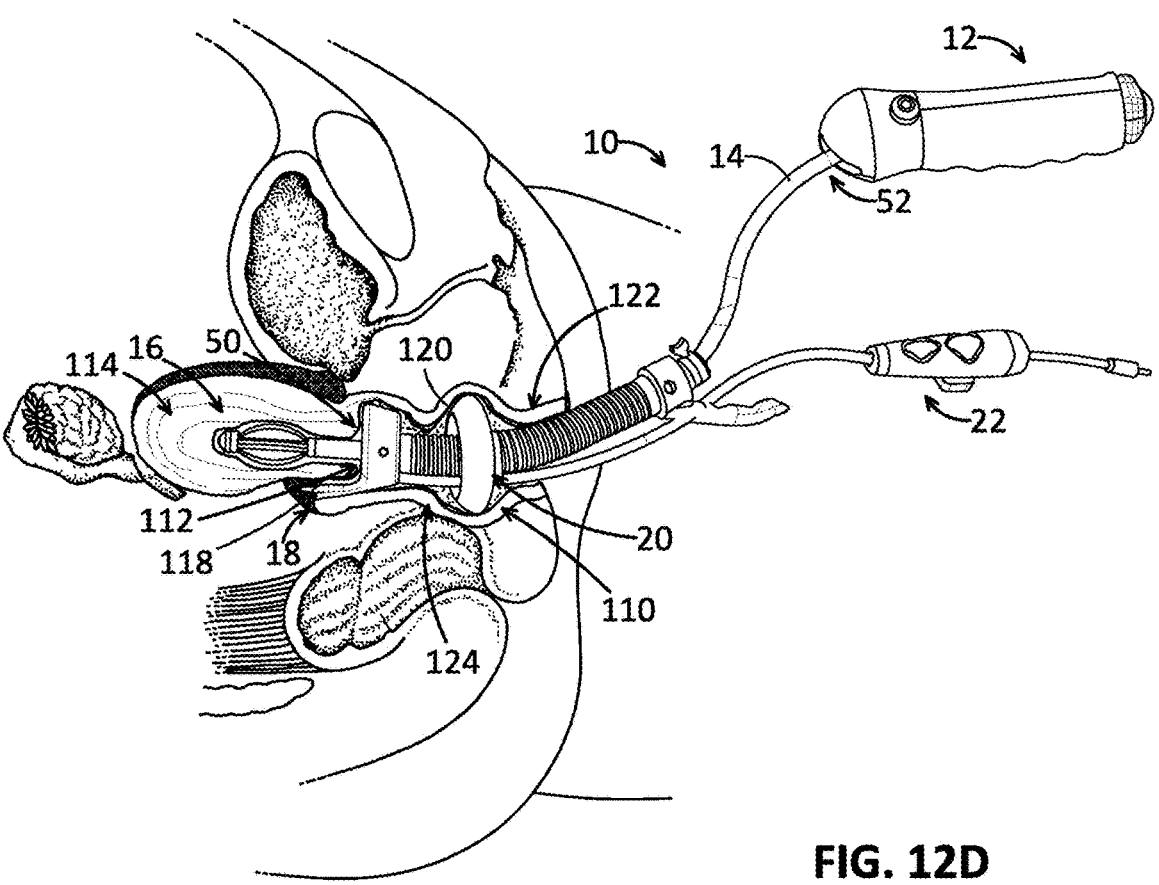

Referring back to FIGS. 1 and 2, the cutting assembly 18 can be slid over the shaft 14 and can be rotatable about the shaft 14. The cutting assembly 18 can include a backstop 74, a tube 76, a cutting handle 78, fasteners 80, and a spring 81. The backstop 74 can be positioned at a first end of the tube 76 and the cutting handle 78 can be positioned at a second, opposite end of the tube 76. The tube 76 can be slid over the shaft 14 and the cutting handle 78 can help maneuver the cutting assembly 18 along and/or around the shaft 14. The fasteners 80 can help fix the cutting assembly 18 in place along the shaft 14. The backstop 74 can receive the cervix 112 and come in contact with the vaginal fornix 118 when the uterine manipulator 10 is in position. The backstop can then be maneuvered in a circular manner to cut around the cervix 112 for detaching the cervix 112 and the uterus 114 from the vagina 110, as shown in FIG. 12D. As shown in FIGS. 10A and 10B, the backstop 74 can include a round cup portion 82 and a cutter 84 extending outward from the cup portion 82. During use, the cutting assembly 18 can be pressed up against the abutment 30 of the tip assembly 16 so that the cup portion 82 extends past the abutment 30 and engages the fornix, stretching and forcing the fornix upward and away from the ureters. The cutter 84 can pierce through the tissue of the fornix, transecting the uterus 114 and the cervix 112 from the top of the vagina 110.

The cutting assembly 18 can be rotated about the shaft 14 (e.g., by the cutting handle 78), allowing the cutter 84 to travel in a circle at the junction of the cervix 112 and the vagina 110 and permitting complete transection of the uterus 114 and the cervix 112 from the vagina 110. The spring 81 can help distribute rotational forces evenly across the tube 76 when the cutting assembly 18 is rotated, for example, to prevent the tube 76 from breaking due to excess torque concentrated along one portion of the tube 76.

The electrical connector assembly 22 can advance the cutter 84 outward from the cup portion 82 to achieve the detachment procedure described above, and can retract the cutter 84 inward to facilitate insertion of the uterine manipulator 10 into the uterus 114 without piercing the vaginal walls 120 prior to proper positioning of the uterine manipulator 10. The electrical connector assembly 22 can provide an electrical connection between the cutter 84 and an electrosurgical unit (not shown) in order to provide hemostasis during the detachment procedure. The electrical connector assembly 22 can include a handle 94, a cap 96, a button 98, tubing 100, 102, and electrical connectors 104, 106. On one end of the electrical connector assembly 22 (i.e., adjacent to the cap 96), the tubing 100 and the electrical connectors 104 can be routed to the electrosurgical unit. On the other end of the electrical connector assembly 22, the tubing 102 and the electrical connectors 106 can be routed to the cutter 84. The electrical connectors 104, 106 can be electrically connected through the button 98 so that current can be routed from the electrosurgical unit to the cutter 84. The electrical connectors 106 can be coupled to the cutter 84 and the button 98 so that pressing the button 98 forward and backward causes the cutter 84 to extend and retract, respectively.

Figure 11:
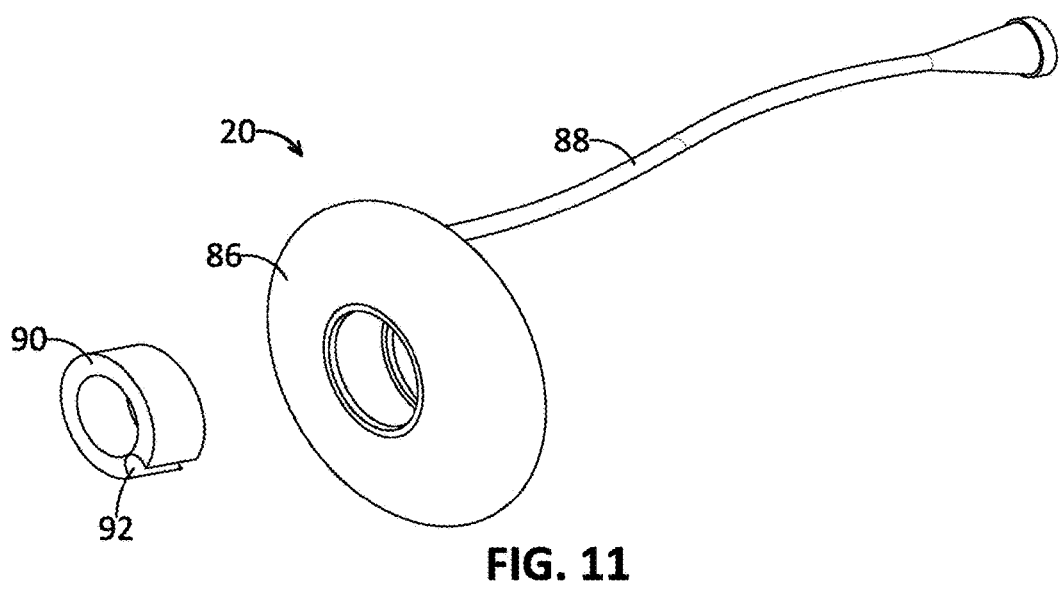
FIG. 11 is a perspective view of a pneumooccluder of the uterine manipulator of FIG. 1.

Referring to FIG. 11, the pneumooccluder 20 can include a balloon 86, a filling tube 88, and a bearing 90. The bearing 90 can be in contact with the tube 76 of the cutting assembly 18, and the balloon 86 can be positioned around the bearing 90. As shown in FIG. 11, the bearing 90 can include an outer groove 92 to allow passage of the electrical connector assembly tubing. During use, the pneumooccluder 20 can be positioned within the vagina 110 when the uterine manipulator 10 is set within the uterus 114. Once in position, the balloon 86 can be inflated via the filling tube 88 (e.g., with air, water, saline, or another fluid) in order to seal the distal vaginal cavity 122 from the proximal vaginal cavity 124. This can help maintain pneumoperitoneum once the incision has been made between the vagina 110 and the cervix 112 (i.e., causing the proximal vaginal cavity 124 to be in fluid communication with the abdominal cavity). As a result of the bearing 90, the shaft 14 and/or the cutting assembly tube 76 can be rotated without requiring rotation of the balloon 86. Because the balloon 86 can be set in place and does not need to be rotated when the shaft 14 or the cutting assembly 18 is rotated, the risk of losing pneumoperitoneum is greatly reduced.

Thus, the uterine manipulator 10 can be inserted into a patient's vagina 110 while in the retracted position, as shown in FIG. 12A. The uterine manipulator 10 can then be further guided through the vagina 110, past the cervix 112, and into the uterus 114, while still in the retracted position, as shown in FIG. 12B. Once set in the uterus 114, the uterine manipulator 10 can be situated into the expanded position, as shown in FIG. 12C, in order to facilitate a secure connection between the uterine manipulator 10 and the uterus 114. Once the uterine manipulator 10 is set within the uterus 114, the pneumooccluder 20 can contact the vaginal wall 120 in order to seal the uterus 114 from the outside environment and the backstop 74 can abut the vaginal fornix 118, causing it to stretch upward. Once the uterine manipulator 10 is situated into the expanded position, the cutter 84 can be extended and the cutting handle 78 can be rotated in order to transect the uterus 114 and the cervix 112 from the top of the vagina 110. The uterine manipulator 10 of the present disclosure and its above-described procedures can thus eliminate the need for a colpotomy incision via laparoscopic tools, as in conventional laparoscopic hysterectomies.

At least one embodiment can include any combination of one or more of the above-described components and/or other conventional uterine manipulator components. The above-described components, such as the cutting assembly 18, the tip assembly 16, and the pneumooccluder 20 can function independently from one another and therefore can be individually incorporated into a uterine manipulator with or without the other components. For example, it may be preferable to include the pneumooccluder 20 as described above with some previous approaches to best execute a specific pelvic procedure.

Figure 13:
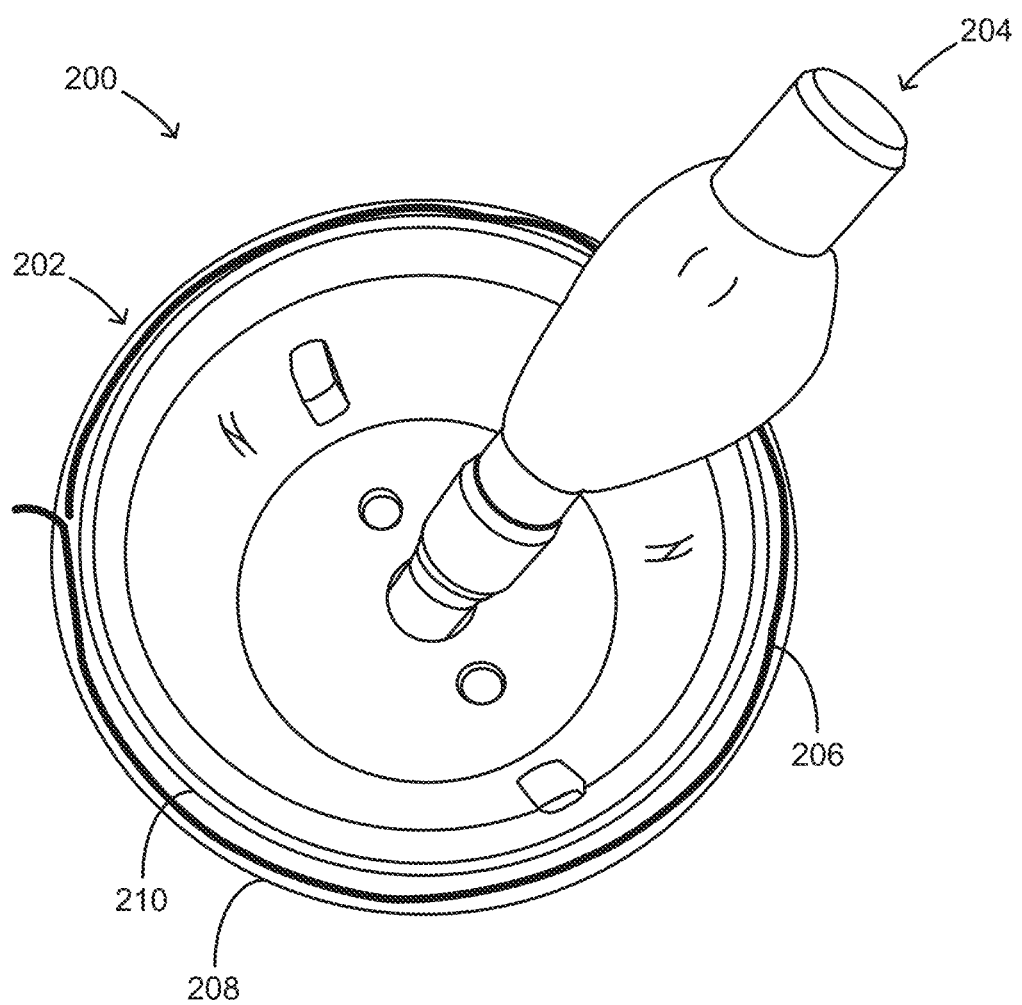
FIG. 13 is a perspective view of a manipulator, cup, and cutting assembly in accordance with the present disclosure.

Referring to FIG. 13, a cutting assembly 200 is illustrated. The cutting assembly 200 can be used with the functional uterine manipulator 10 of the preceding figures or can be used with other systems. The cutting assembly 200 includes a cup portion 202 and an expansion tip 204 extending therethrough. As illustrated in FIG. 13, the expansion tip 204 can be a balloon-type design or other configurations, such as described above. Associated with the cup portion 202 is a cutter or cutter wire 206. The cup portion 202 is designed to engage the cervix 112, such as previously described. The cutter 206 is formed as a narrow wire, with a looped tip, embedded between two grooves 208, 210 on the cup portion 202 (that is, around the circumference of the cup portion 202).

Figure 15A:
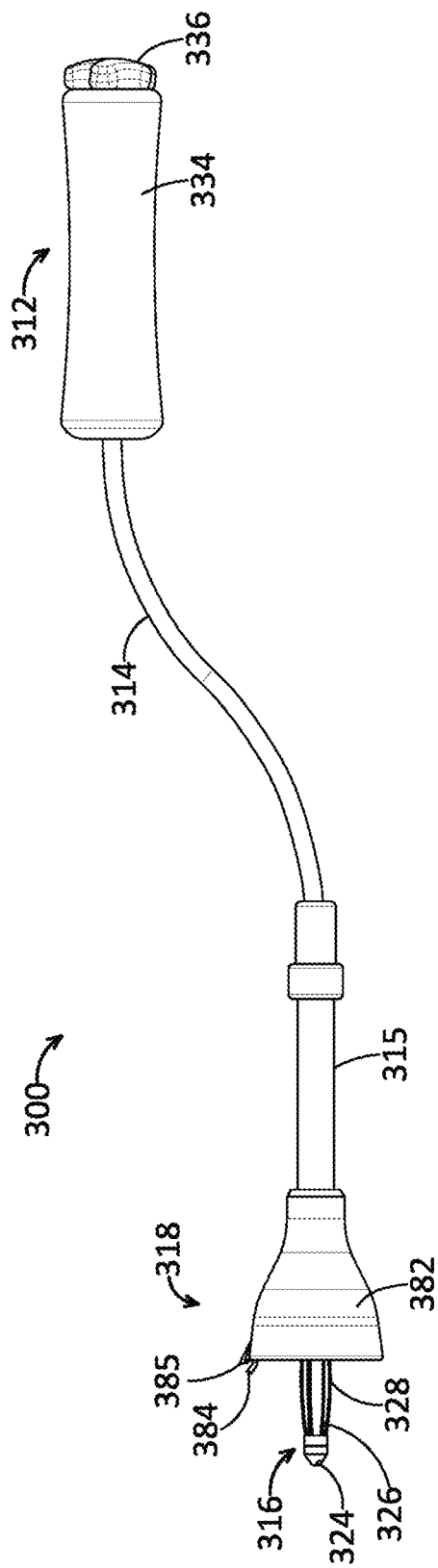
FIGS. 15A-15B are side views of a uterine manipulator in accordance with the present disclosure.
Figure 15B:
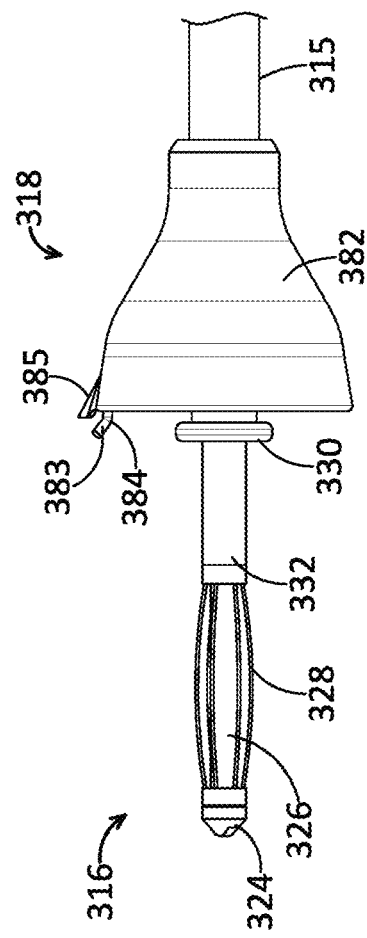

FIGS. 15A-15B illustrate another uterine manipulator 300. The uterine manipulator 300 can include a handle 312, a shaft 314, a tip assembly 316, and a cutting assembly 318. Unless otherwise stated, the elements of the uterine manipulator 300 can be similar in function and structure to those of the above-described uterine manipulator 100 of the previous figures. The uterine manipulator 300 can incorporate any of the above-described elements of the previous figures. For example, the tip assembly 316 can include an expansion tip 324, a tip shaft 326, umbrella-like expansion elements 328, an abutment 330, and a tip housing 332. The handle 312 can include a handle housing 334 and an expansion actuator 336.

Twisting or rotating the expansion actuator 336 in a first direction causes the expansion elements 328 to compress and expand outward circumferentially, situating the tip assembly 316 into the expanded position. Twisting or rotating the expansion actuator 336 in a second, opposite direction causes the expansion elements 328 to retract back into tension and lengthen, situating the tip assembly 316 into the retracted position.

The cutting assembly 318 can be rotatable about the shaft 314. More specifically, as shown in FIGS. 15A-15B, the uterine manipulator 300 can include a flexible shaft portion 315 along which the cutting assembly 318 can slide laterally and/or rotated for proper positioning or operation. The cutting assembly 318 can include a cup portion 382 and a cutter or cutter wire 384. Similar to the cutter 206 of FIG. 13, the cutter 384 can be formed as a narrow wire, with a looped tip 383, embedded between grooves (not shown) on the cup portion 382. In addition, the cup portion 382 can include a projection 385 to assist an operator in locating the cutter 384 during an operation, to help shield the cutter 384 during insertion of the uterine manipulator 300, and/or to help push the cutter 384 through the vaginal tissue.

Figure 14:
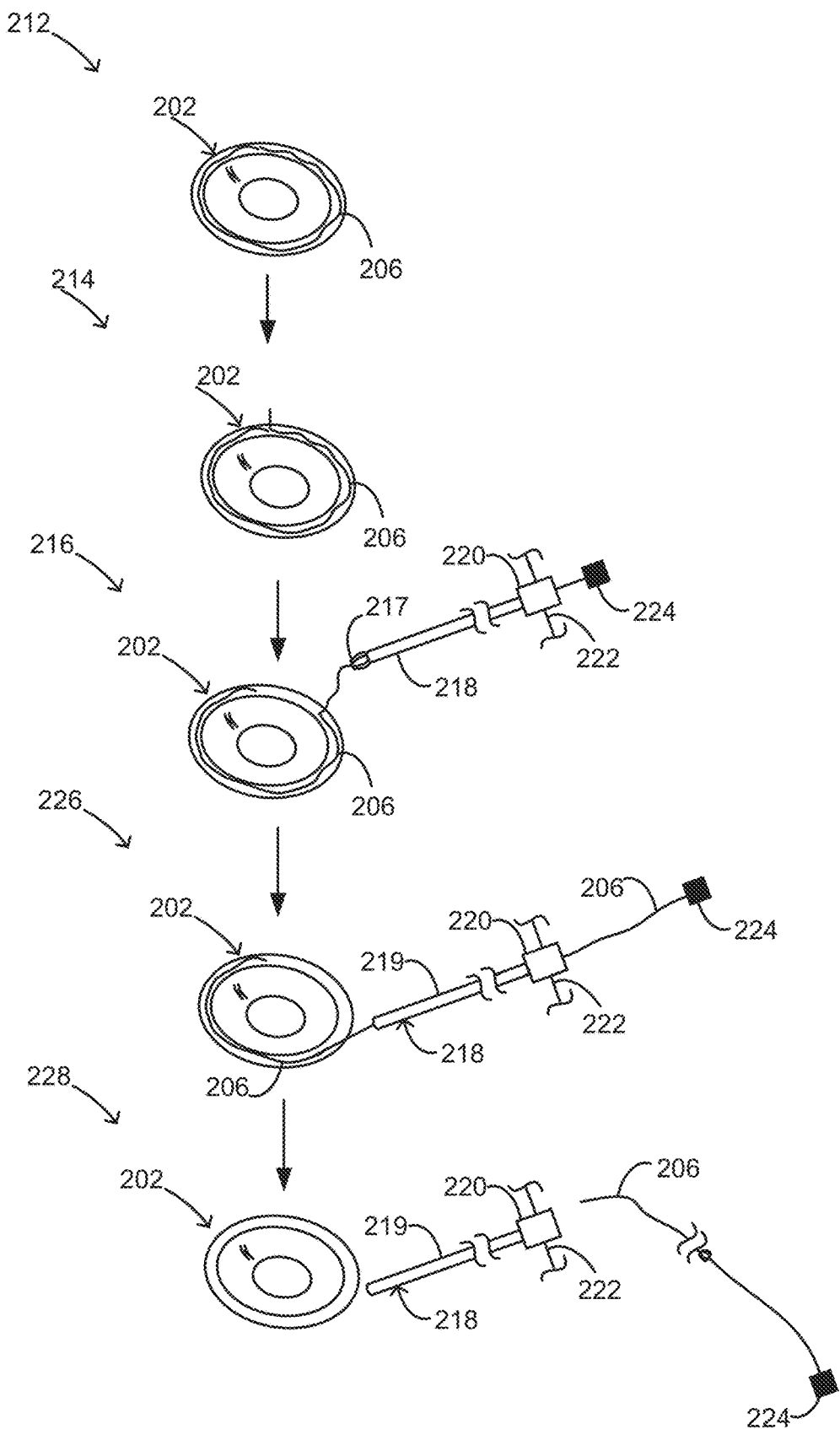
FIG. 14 is a series of views showing use of the cutting assembly of FIG. 13 in accordance with the present disclosure.

Referring to FIG. 14, the cutter 206 (or the cutter 384) is preset in a stored position 212 between the grooves 208, 210 (for example, when the uterine manipulator 100/300 is being inserted into a patient's uterus 114). The cutter wire can be secured between the grooves 208, 210 by small, thin bridges (not shown) around the edge of the cup portion 202, with the looped tip of the cutter 206 extending outward from the grooves 208, 210 at a 12 o'clock position. The bridges can be thin enough that they can be easily broken by pulling the cutter 206 against the bridges with sufficient force. The cutter 206 is designed to move from the stored position 212 to an extended position 214 where the cutter 206 can be pushed through the top of the vagina (for example, with the help of the projection 383 of cup portion 382) after the cup portion 202 has been positioned at a juncture between the cervix 112 and the vagina 110 (for example, the vaginal fornix 118). In a further extended position 216, the cutter 206 can be pulled in by a laparoscopic instrument 218, or "wand," that is introduced laparoscopically. The instrument 218 includes a trocar 220 that extends through the skin 222 to present a handle 224 to a clinician. The instrument 218 also includes a small grasper 217 at its proximal end that can grasp or engage with the looped tip of the cutter 206. Using the handle 224, the instrument 218 is directed around the cup portion 202 and, as a result, pulls the cutter 206 at position 226. As the cutter 206 makes contact with tissue at the juncture of the vagina 110 and cervix 112, the tissue is cut, thus separating the vagina 110 from the cervix 112 and uterus 114. At a final position 228, for example, once the cutter 206 has been pulled around the circumference of the cup portion 202, the cutter 206 can be separated from the cup portion 202. The laparoscopic instrument, with the entire cutter 206, can then be removed through a laparoscopic port at the skin 222.

The inner groove 210 of the cup portion 202 can be taller than the outer groove 208 to prevent the cutter 206 from being pulled inward (instead of upward or outward) as the instrument 218 pulls the cutter 206. In addition, the laparoscopic instrument 218 can include an outer insulation cover 219 that is pushed forward while the cutter 206 is pulled out of the grooves 208, 210. That is, the cutter 206 is pulled into or received in the laparoscopic instrument 218 so that the cutter 206 is covered by the laparoscopic instrument 218 during operation, thereby enhancing safety given that the cutting wire or blade (which can be carrying electrical current, as described below) is not exposed at any given time.

The cutter 206 can either cut the vagina without electrical current ("cold") or with an electrical current, based on surgeon preference. For example, a distal end of the laparoscopic instrument 218 can connect to an electrosurgical unit (not shown) or electrical connector assembly, which can conduct monopolar or bipolar current. Accordingly, once the laparoscopic instrument 218 grasps the cutter 206, current is passed through the instrument 218 and to the cutter wire 206. Different operations can be conducted based on monopolar or bipolar configurations. For example, in a monopolar configuration, the cutter 206 can be pulled out of the cup portion 202 along its entire circumference and removed via the laparoscopic instrument 218 (as described above with reference to FIG. 14) while the cup portion 202 remains fixed to a shaft (such as shaft 14 or 314). More specifically, the cup portion 202 is not rotated about the shaft during this operation. Power during monopolar operation can be relatively high, such as about 100 watts.

In a bipolar configuration, the cutter 206 can be a shorter wire than the monopolar configuration, for example, about 2 centimeters (cm) to about 3 cm. The cutter 206 can be pulled through the vaginal tissue by the laparoscopic instrument 218, remaining at the 12 o'clock position, and then the cup portion 202 can be rotated about the shaft as the cutter 206 is held in place. One pole of the bipolar current can be through the laparoscopic instrument 218 (connected to the cutter wire 206) and the other pole can be through the cup portion 202.

In at least one embodiment, the shorter cutter 206 can be held between the grooves 208, 210 by a small ball (not shown) at a distal end of the cutter 206. The ball can help the cutter 206 slide around the circumference of the cup portion 202 but also prevents the entire cutter 206 from being pulled out from between the grooves 208, 210 as the laparoscopic instrument 218 pulls the cutter 206. Once the cutter 206 has traversed the entire circumference of the cup portion 202, a break or opening (not shown) between the grooves 208, 210 can allow the ball to be pulled out from the cup portion 202 and into the laparoscopic instrument 218 for removal. This ball configuration can be used with bipolar or monopolar applications. In bipolar applications, a small metal lining inside of the grooves 208, 210 can electrically connect the cup portion 202 to the ball (which is electrically connected to the laparoscopic instrument 218).

The uterine manipulator 10, 300, 400, or at least one or more components of the uterine manipulator 10, 300, can be used with orifice-assisted small incision surgeries (OASIS).

In such surgeries, instrumentation can be inserted through a patient's belly button as well as the patient's vagina 110. The optical axis (e.g., of a laparoscope inserted through the belly button) can be decoupled from the operative axis (e.g., of a surgical tool inserted through the vagina 110). The uterine manipulator 10, 300 can include an extension tool to assist with OASIS procedures.

The present disclosure has described one or more preferred embodiments.

However, it should be appreciated that many equivalents, alternatives, variations, and modifications, aside from those expressly stated, are possible and within the scope of the invention.

The invention claimed is:

1. A uterine manipulator, comprising:
   a shaft including a proximal end, and a distal end;
   a manipulator handle coupled to the proximal end of the shaft;
   an intrauterine device coupled to the distal end of the shaft, the intrauterine device configured for being expanded within a uterus;
   a cutting assembly rotatably disposed about the shaft, the cutting assembly including:
      a tube rotatably disposed about the shaft;
      a cutting handle coupled to a proximal portion of the tube;
      a cup to receive at least a portion of a fornix of a patient, the cup being coupled to a distal portion of the tube; and
      a retractable cutter extending distally with respect to the cup, the retractable cutter being movable from a retracted position to an extended position, wherein the retractable cutter extends distally beyond the cup when in the extended position, wherein the cutting assembly can be rotated about the shaft by the cutting handle to allow the retractable cutter to travel in a circle at a junction of a cervix and a vagina to permit transection of a uterus and a cervix from a vagina; and
   an electrical connector assembly configured for electrically coupling an electrosurgical unit to the retractable cutter, the electrical connector assembly including:
      a handle separate from the cutting handle;
      an electrical connector mechanically and electrically coupled between the handle and the retractable cutter external to the tube; and
      an actuator carried by the handle and coupled to the electrical connector, wherein manipulation of the actuator causes the retractable cutter to move between the extended position and retracted position.

2. The uterine manipulator of claim 1, wherein the retractable cutter passes through a channel defined in the cup, and further wherein the retractable cutter slides with respect to the channel defined in the cup when it is advanced and retracted.

3. The uterine manipulator of claim 1, wherein the the electrical connector assembly is configured for electrically coupling the electrosurgical generator to the retractable cutter through the actuator.

4. The uterine manipulator of claim 1, wherein the cutting handle, tube, retractable cutter, and cup are configured to rotate about the shaft in unison.

5. The uterine manipulator of claim 1, wherein the retractable cutter includes a blade.

6. An electrosurgical system comprising:
   the uterine manipulator of claim 1; and
   the electrosurgical unit coupled to the uterine manipulator via the electrical connector assembly, wherein current can be selectively routed from the electrosurgical unit to the retractable cutter.

7. The uterine manipulator of claim 1, further comprising a pneumo-occluder coupled to the distal portion of the tube.

8. The uterine manipulator of claim 7, wherein the pneumo-occluder includes:
   a bearing coupled to the distal portion of the tube; and
   a balloon rotatably coupled to the distal portion of the tube via the bearing.

9. The uterine manipulator of claim 8, wherein the electrical connector is disposed between the tube and the balloon.

10. The uterine manipulator of claim 9, wherein the bearing has an outer groove that allows passage of the electrical connector.

11. The uterine manipulator of claim 1, wherein the actuator comprises a button.

12. The uterine manipulator of claim 1, wherein the actuator is a slidable actuator, wherein advancing the slidable actuator distally and proximally causes the retractable cutter to be in the extended position and retracted position, respectively.

13. The uterine manipulator of claim 1, wherein the cutting assembly further includes a spring disposed along the tube, wherein the spring is configured for distributing rotational forces evenly across the tube when the cutting assembly is rotated about the shaft.

14. The uterine manipulator of claim 1, wherein the electrical connector assembly further includes tubing mechanically coupled between the handle and the cup, the electrical connector being slidably disposed within the tubing.

15. A uterine manipulator, comprising:
   a shaft including a proximal end, and a distal end;
   a manipulator handle coupled to the proximal end of the shaft;
   an intrauterine device coupled to the distal end of the shaft, the intrauterine device configured for being expanded within a uterus;
   a cutting assembly rotatably disposed about the shaft, the cutting assembly including:
      a tube rotatably disposed about the shaft;
      a cutting handle coupled to a proximal portion of the tube;
      a cup to receive at least a portion of a fornix of a patient, the cup being coupled to a distal portion of the tube; and
      a retractable cutter extendable distally with respect to the cup, the retractable cutter being movable from a retracted position to an extended position, wherein the retractable cutter extends distally beyond the cup when in the extended position, wherein the cutting assembly can be rotated about the shaft by the cutting handle to allow the retractable cutter to travel in a circle at a junction of a cervix and a vagina to permit transection of a uterus and a cervix from a vagina;
   an outer tubular member surrounding the tube of the cutting assembly to permit the cutting assembly to be rotated within the outer tubular member while the outer tubular member is held stationary;
   a pneumooccluder disposed on the outer tubular member, the pneumooccluder including an inflatable member coupled to a filling tube;

an electrical conductor extending proximally from the retractable cutter at a location that is radially outward with respect to an exterior surface of the tube of the cutting assembly and radially inward with respect to the pneumooccluder;

a further tubular member extending along a length of the manipulator, the further tubular member being located radially outwardly with respect to an exterior surface of the tube of the cutting assembly and radially inward with respect to the pneumooccluder, wherein the electrical conductor passes through a lumen defined at least in part by the further tubular member;

a mechanical actuator mechanically coupled to the retractable cutter, the mechanical actuator being operable to mechanically advance and retract the cutter between the extended position and retracted position; and an electrical connector to electrically couple an electrosurgical unit to the retractable cutter through the electrical conductor.

16. The uterine manipulator of claim 15, wherein the retractable cutter passes through a channel defined in the cup, and further wherein the retractable cutter slides with respect to the channel defined in the cup when it is advanced and retracted.

17. The uterine manipulator of claim 15, wherein the retractable cutter includes a blade.

* * * * *